(12) United States Patent
Gehling et al.

(10) Patent No.: US 6,899,700 B2
(45) Date of Patent: May 31, 2005

(54) THERAPEUTIC AGENT DELIVERY TAMPON

(75) Inventors: Steven Craig Gehling, Oshkosh, WI (US); Charles Christopher Keely, Neenah, WI (US); Jeffrey Dean Lindsay, Appleton, WI (US); Kimberly Marie Geiser, Appleton, WI (US); David William Koenig, Menasha, WI (US); Bernard Joseph Minerath, Oshkosh, WI (US); Barbara Jo Dvoracek, Appleton, WI (US); David John Tyrrell, Appleton, WI (US); Duane Gerard Krzysik, Appleton, WI (US)

(73) Assignee: Kimberly-Clark Worldwide, Inc., Neenah, MI (US)

( * ) Notice: Subject to any disclaimer, the term of this patent is extended or adjusted under 35 U.S.C. 154(b) by 0 days.

(21) Appl. No.: 10/027,269

(22) Filed: Dec. 21, 2001

(65) Prior Publication Data

US 2003/0045829 A1 Mar. 6, 2003

Related U.S. Application Data

(60) Provisional application No. 60/315,882, filed on Aug. 29, 2001.

(51) Int. Cl.[7] ............................................... A61M 31/00
(52) U.S. Cl. .................. 604/285; 604/385.17; 604/904; 604/286; 604/11; 604/515; 424/400; 424/422; 424/76.1
(58) Field of Search ................................. 604/363, 381, 604/382.18, 382.17, 904, 286, 11, 285, 515; 424/431, 400, 422, 76.1

(56) References Cited

U.S. PATENT DOCUMENTS

| | | | | |
|---|---|---|---|---|
| 2,110,962 A | * | 3/1938 | Munro | ........................ 604/11 |
| 3,338,992 A | | 8/1967 | Kinney | |
| 3,341,394 A | | 9/1967 | Kinney | |

(Continued)

FOREIGN PATENT DOCUMENTS

| | | |
|---|---|---|
| AU | 1999 41153 A1 | 6/2000 |
| CH | 561 058 | 4/1975 |
| DE | 30 38 192 A1 | 12/1982 |
| EP | 1 051 956 A1 | 11/2000 |
| WO | WO 99/17813 A1 | 4/1999 |
| WO | WO 99/56681 A2 | 11/1999 |
| WO | WO 00/51445 A2 | 9/2000 |
| WO | WO 01/60299 A1 | 8/2001 |

OTHER PUBLICATIONS

Patent Abstracts of Japan 02212431 A: Description of Watanabe Tadahiko/Nippon Shakai Iryo, "Tampon for Improving Metrorrhagia and Leukorrhea.".

Patent Cooperation Treaty Search Report from the International Search Authority, International Application No. PCT/US 02/17605 dated Dec. 12, 2002.

Hoffmann, Allan S. and Tapas K. De, "Bioadhesive Polyacrylic Acid Nanoparticles: Preparation, Characterization, Drug Loading and Release," Controlled Release Society, Inc., Proceedings Book, *The 26th International Symposium on Controlled Release of Bioactive Materials*, Jun. 20–23, 1999, pp. 315–316.

(Continued)

*Primary Examiner*—Jacqueline F. Stephens
(74) *Attorney, Agent, or Firm*—Randall W. Fieldhack

(57) ABSTRACT

A tampon adapted to deliver a therapeutic agent includes a body having a proximal end and a distal end. The body includes an absorbency zone adjacent the distal end, wherein the absorbency zone includes absorbent material; an application zone adjacent the proximal end and spaced apart from the distal end; and a therapeutic agent positioned substantially within the application zone. A method produces a device for delivering a therapeutic agent. The method includes manufacturing a tampon having a body with a distal end, a proximal end, an absorbency zone adjacent the distal end, and an application zone adjacent the proximal end; and locating a therapeutic agent substantially within the application zone.

14 Claims, 1 Drawing Sheet

U.S. PATENT DOCUMENTS

| | | | | |
|---|---|---|---|---|
| 3,393,678 | A | * | 7/1968 | Pacini .................. 604/286 |
| 3,490,454 | A | * | 1/1970 | Goldfarb et al. |
| 3,502,538 | A | | 3/1970 | Peterson |
| 3,502,763 | A | | 3/1970 | Hartmann |
| 3,542,615 | A | | 11/1970 | Dobo et al. |
| 3,559,646 | A | * | 2/1971 | Mullan |
| 3,683,912 | A | * | 8/1972 | Olson et al. |
| 3,692,618 | A | | 9/1972 | Dorschner et al. |
| 3,699,965 | A | * | 10/1972 | Dostal |
| 3,802,817 | A | | 4/1974 | Matsuki et al. |
| 3,849,241 | A | | 11/1974 | Butin et al. |
| 4,286,596 | A | * | 9/1981 | Runinstein |
| 4,309,997 | A | | 1/1982 | Donald |
| 4,318,405 | A | * | 3/1982 | Sneider |
| 4,335,720 | A | * | 6/1982 | Glassman |
| 4,340,563 | A | | 7/1982 | Appel et al. |
| 4,374,522 | A | * | 2/1983 | Olevsky |
| 4,488,928 | A | | 12/1984 | Ali Khan et al. |
| 4,510,020 | A | | 4/1985 | Green et al. |
| 4,726,976 | A | | 2/1988 | Karami et al. |
| 4,846,824 | A | | 7/1989 | Lassen et al. |
| 4,983,392 | A | | 1/1991 | Robinson |
| 5,096,539 | A | | 3/1992 | Allan |
| 5,192,802 | A | | 3/1993 | Rencher |
| 5,273,521 | A | * | 12/1993 | Peiler et al. |
| 5,295,984 | A | | 3/1994 | Contente et al. |
| 5,447,499 | A | * | 9/1995 | Allaire et al. ............ 602/42 |
| 5,527,534 | A | | 6/1996 | Myhling |
| 5,540,979 | A | | 7/1996 | Yahiaoui et al. |
| 5,585,277 | A | | 12/1996 | Bowie et al. |
| 5,652,194 | A | | 7/1997 | Dyer et al. |
| 5,840,055 | A | * | 11/1998 | Sgro |
| 5,891,126 | A | | 4/1999 | Osborn, III et al. |
| 5,984,888 | A | | 11/1999 | Nielsen et al. |
| 5,990,377 | A | | 11/1999 | Chen et al. |
| 6,036,666 | A | * | 3/2000 | Peiler et al. |
| 6,086,909 | A | | 7/2000 | Harrison et al. |
| 6,261,679 | B1 | | 7/2001 | Chen et al. |
| 6,359,191 | B1 | * | 3/2002 | Rusch et al. |

OTHER PUBLICATIONS

Hoffman, Allan S. and Guohua Chen, Xiangdong Wu, Zhongli Ding, "Graft Copolymers of PEO–PPO–PEO Triblock Polyethers on Bioadhesive Polymer Backbones for Use as Drug Delivery Carriers," American Chemical Society, Abstracts of Papers, Part 2, $213^{th}$ ACS National Meeting, Apr. 13–17, 1997, PMSE–167.

Gray, Henry, Anatomy of the Human Body, vol. II, Thirtieth American Edition, published by Lea and Febiger, 1985, pp. 1566–1586.

Park, Haesun and Joseph R. Robinson, "Physico–Chemical Properties of Water Insoluble Polymers Important to Mucin/Epithelial Adhesion," Journal of Controlled Release, 2, published 1985, pp. 47–57.

Lee, Chi–Hyun and Yie W. Chien, "Development and Evaluation of a Mucoadhesive Drug Delivery System for Dual–Controlled Delivery of Nonoxynol–9," Journal of Controlled Release, vol. 39, published 1996, pp. 93–103.

Inoue, Tadaaki, Guohua Chen and Allan S. Hoffman, "A Hydrophobically Modified Bioadhesive Polymeric Carrier for Controlled Drug Delivery to Mucosal Surfaces," Journal of Bioactive and Compatible Polymers, vol. 13, No. 1, published Jan. 1998, pp. 50–64.

* cited by examiner

THERAPEUTIC AGENT DELIVERY TAMPON

RELATED APPLICATIONS

This application claims the priority of provisional patent application, Ser. No. 60/315,882, filed Aug. 29, 2001.

BACKGROUND

Many disease states and physiological conditions can occur in a woman, including symptoms associated with premenstrual syndrome, menstruation, and menopause. These symptoms may include dysmenorrhea (menstrual cramping), irritability, water retention, moodiness, depression, anxiety, skin changes, headaches, breast tenderness, tension, weight gain, cravings, fatigue, and hot flashes. Symptoms of conditions can include itching and other associated sensory maladies.

Many of these symptoms are due to changes in hormonal levels throughout the menstrual cycle. Menstrual cramping is associated with increased levels of prostaglandin F2α, prostaglandin E2, and in some cases leukotrienes in the endometrium and menstrual fluid. These eicosinoids lead to restricted blood flow to the uterus and increased uterine contractions, causing pain.

One symptom is dysmenorrhea, which is the occurrence of painful uterine cramps during menstruation that affects a large number of post-pubescent women. The pain of dysmenorrhea originates in the uterus. Various analgesics can be effective in limiting the pain from dysmenorrhea; some have used orally-delivered analgesics, while others have searched for alternative analgesic delivery methods. Attempts have been made to deliver analgesics in the vicinity of the cervix and the vaginal mucosa using various vaginally-inserted devices and methods. A similar situation exists with many other disease states and physiological conditions.

Disposable absorbent devices for the absorption of human exudates are widely used. These disposable absorbent devices typically have a mass of absorbent formed into a desired shape, which is typically dictated by the intended consumer use. In the area of a catamenial tampon, the disposable absorbent article is intended to be inserted in a body cavity for absorption of the body fluids generally discharged during a woman's menstrual period. One convenient way to position such absorbent tampons into a body cavity is through the use of an applicator.

Because dysmenorrhea can occur in conjunction with menstruation, some have tried to combine an analgesic with a tampon such that the tampon can perform two functions: absorption and treatment.

U.S. Pat. No. 6,086,909 describes a device and method for treatment of dysmenorrhea using a tampon as a therapeutic agent delivery system. The embodiments described therein each emphasize the location of the therapeutic agent and carrier portion of the therapeutic agent delivery system as being in close proximity to the uterus, specifically at the cervix or posterior fornix of the vaginal cavity. To accomplish this, the therapeutic agent delivery portion of the tampon is in each case located at the distal or cervical end of the tampon as a means to locate the therapeutic agent in proximity to the cervix. Various embodiments covering the structure of the distal end of a tampon, including tubes and porous materials such as foam cups, are presented in an attempt to deliver the therapeutic agent as well as to manage the menses into the absorbent structure of the tampon.

SUMMARY OF THE INVENTION

One difficulty in using orally-delivered analgesics is that oral doses of analgesics large enough to be efficacious can lead to adverse side effects, thus limiting the actual dose of the analgesics. Limiting doses in an attempt to limit those side effects results in an insufficient amount of analgesic delivered to the uterus. In addition, the use of analgesics delivered by alternative means, including through the use of tampons, can still cause side effects because of the inherent nature of the analgesics.

The difficulty in using a tampon as a therapeutic agent delivery system is in managing both the transfer of the therapeutic agent out of the tampon, and the transfer of menses into the tampon. For example, if the therapeutic agent formulation is generally hydrophilic, the therapeutic agent formulation will tend to absorb into the tampon, or be carried by the menses into the tampon. If the therapeutic agent formulation is generally hydrophobic, the therapeutic agent formulation will tend to block the absorbency of the tampon, especially if the therapeutic agent is applied to the distal end of the tampon, which is the end closest to the source of menses.

As described above, the prior art uses various multi-component structures such as foam cups or tubes located at the tip or distal end of the tampon in an attempt to separate the absorbent and therapeutic agent delivery functions. These structures are required to direct the menses into the tampon and away from the therapeutic agent delivery system.

Such multi-component therapeutic agent delivery systems can lead to a number of problems. First, the absorbent function of the tampon is less reliable because menses must flow through an intermediate system rather than contacting the absorbent component directly. Second, such multi-component systems can be less safe because removal of the entire tampon from the body cavity relies on the various components of the tampon remaining intact and connected. Third, multi-component systems are more difficult and more expensive to manufacture. Finally, the incorporation of porous foam or other additional components on the distal end of a tampon is disadvantageous to applicator style tampons, because tampon applicator tube petals can adversely interact with the additional components during tampon insertion, thus increasing the potential for mechanical deterioration or separation of the additional components from the tampon as they pass through the petal openings.

The present invention overcomes these problems by providing a tampon that delivers a therapeutic agent while minimizing the effect on the absorbency of the tampon. By locating the therapeutic agent delivery system at the proximal or string end of the tampon, the functionality of the tampon is less hindered.

This invention describes a therapeutic agent delivery system in cooperation with a tampon, such that the absorbent functionality of the tampon is preserved in addition to providing a therapeutic agent delivery system that is integral with or associated with the proximal or string end of the tampon. The therapeutic agent delivery system, including any therapeutic agents and carrier components, can include any therapeutic agent that will be absorbed into the body through the vaginal epithelium for the purpose of treating a condition. More specifically, a therapeutic agent may be used for the purpose of treating dysmenorrhea. In one embodiment, the therapeutic agent and its delivery system are applied to the outer surface of the tampon and predominantly to the surfaces that are in contact with the vaginal epithelium. Other embodiments would provide a reservoir of a therapeutic agent incorporated into the tampon to provide mechanisms by which varying doses are delivered, or a means to provide release of the therapeutic agent over the duration of contact with the vaginal epithelium.

More specifically, the invention provides a device adapted to deliver a therapeutic agent, the device including a body having a proximal end and a distal end, the body including an absorbency zone adjacent the distal end, wherein the absorbency zone includes absorbent material; an application zone adjacent the proximal end and spaced apart from the distal end; and a therapeutic agent positioned substantially within the application zone. The invention also provides a method for producing a device for delivering a therapeutic agent, the method including manufacturing a device having a body with a distal end, a proximal end, an absorbency zone adjacent the distal end, and an application zone adjacent the proximal end; and locating a therapeutic agent substantially within the application zone.

The present invention provides several attributes that are advantageous to a tampon therapeutic agent delivery system. Specifically, the present invention provides initial separation between the greater amount of menses expected at the distal end of the tampon, and the therapeutic agent delivery system located at the opposite or proximal end of the tampon. This initial physical separation of the menses from the delivery system therapeutic agents is advantageous to reduce the dilutive effects of the menses on the therapeutic agents, and thereby potentially allowing a more efficient delivery of the therapeutic agent dose to be administered. The therapeutic agent delivery system is also expected to be less encumbered as menses saturates the tampon.

Product safety concerns by this invention are reduced, since the integrity of the tampon during use is similar to current product forms. The potential for leaving a portion of the therapeutic agent and/or therapeutic agent carrier system in the vaginal cavity during insertion or removal of the tampon is reduced in this invention because the therapeutic agent delivery system is located at the proximal end of the tampon, and additional therapeutic agent delivery components, such as tubes and foam materials, identified in the prior art are absent in this invention.

A further advantage of one embodiment of this invention is made possible by the use of the applicator insertion tube as a mechanism to provide pressure to the proximal end of the tampon during the process of insertion, whereby the insertion pressure could be used to advantageously cause the therapeutic agent to migrate out to the outer surface of the tampon, such that the therapeutic agent is in the proximity of the vaginal epithelium. Another embodiment provides a means to rupture an encapsulated therapeutic agent device during insertion or withdrawal whereby the therapeutic agent can be kept unaltered within the encapsulated device until use.

Product costs of this disclosed invention would also be advantageous over prior art since the product has fewer components and the product is also compatible with known and existing tampon manufacturing processes.

Other objects and advantages of the present invention will become more apparent to those skilled in the art in view of the following description and the accompanying drawings.

DETAILED DESCRIPTION OF THE PREFERRED EMBODIMENTS

Figure 1:
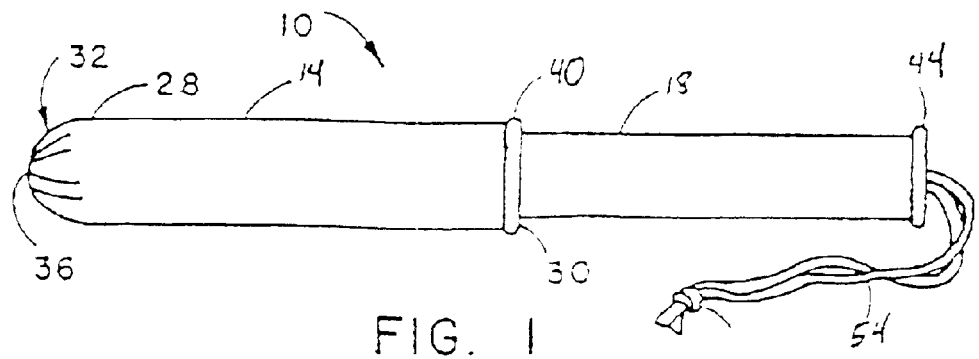
FIG. 1 is a perspective view of a two piece tampon applicator.

The invention as described herein will be described for exemplary purposes using a tampon as an example of a product. The invention, however, applies equally to other forms of products and should not be limited to the example described herein. In addition, although the example described includes a tampon with absorbent material, a product without absorbent material is also contemplated within the invention. Also contemplated is the use of the invention described herein in conjunction with non-catamenial feminine products such as incontinence products, including female incontinence inserts.

As used herein the term "nonwoven fabric or web" means a web having a structure of individual fibers or threads that are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard ("osy") or grams per square meter ("gsm") and the fiber diameters useful are usually expressed in microns. Basis weights can be converted from osy to gsm simply by multiplying the value in osy by 33.91.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615. Spunbond fibers are quenched and generally not tacky when deposited onto a collecting surface. Spunbond fibers are generally continuous and have average diameters frequently larger than 7 microns, typically between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers that may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer shall include all possible geometrical configurations of the material. These configurations include, but are not limited to isotactic, syndiotactic and random symmetries.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. The phrase "naturally hydrophobic" refers to those materials that are hydrophobic in their chemical composition state without additives or treatments affecting the hydrophobicity. It will be recognized that hydrophobic materials may be treated internally or externally with treatments such as surfactants and the like to render them hydrophilic.

The term "surface" and its plural generally refer herein to the outer or the topmost boundary of an object.

As used herein, the phrase "absorbent article" refers to devices which absorb and contain body fluids, and more specifically, refers to devices which are placed against or near the skin, or against or near the vaginal vault epithelium, to absorb and contain the various fluids discharged from the body.

The term "disposable" is used herein to describe absorbent articles that are not intended to be laundered or otherwise restored or reused as an absorbent article after a single use.

Figure 2:
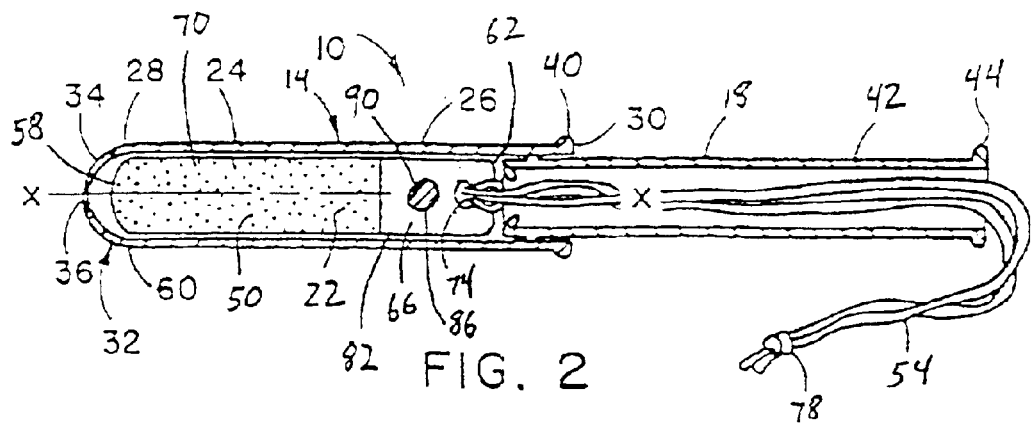
FIG. 2 is a cross-sectional view of the tampon applicator shown in FIG. 1.

FIGS. 1–2 illustrate a tampon applicator 10, including a first member 14 and a second member 18, which is designed to house a catamenial tampon 22 and provide a comfortable means of inserting the tampon 22 into a woman's vagina.

The tampon applicator 10 includes a first member 14 and a second member 18. The first member 14 can be in the form of a spirally wound, convolutely wound or longitudinally seamed hollow tube which is formed from paper, paperboard, cardboard, other suitable material, or a combination thereof. The first member 14 can also be seamlessly formed of plastic. Any plastic in the first member 14 is preferably polyethylene, but may be polypropylene or other suitable plastic. The first member 14, also commonly referred to as an outer tube, can be of any suitable dimensional arrangement. For example, the first member 14 may be fairly rigid and have a relatively small diameter of about 10 mm to about 20 mm. The first member 14 has a wall 24 that may have a predetermined thickness of about 0.2 mm to about 0.6 mm. The wall 24 can be constructed from a single ply of material or be formed from two or more plies which are bonded together to form a laminate. The use of two or more plies or layers enables the manufacture to use certain material in the various layers that can enhance the performance of the tampon applicator 10. When two or more plies are utilized, all the plies can be spirally wound, convolutely wound or longitudinally seamed to form an elongated cylinder. The wall 24 can be constructed using a smooth thin ply of material on the outside or exterior surface 26 which surrounds a coarser and possibly thicker ply. When the wall 24 contains at least three plies, the middle ply can be the thicker ply and the interior and exterior plies can be smooth and/or slippery to facilitate expulsion of the tampon 22 and to facilitate insertion of the first member 14 into a woman's vagina, respectively. By sandwiching a thick, coarser ply of material between two thin, smooth plies, an inexpensive first member 14 can be provided that is very functional. The wall 24 should contain one to four plies, although more plies can be utilized if desired.

The plies forming the wall 24 can be held together by an adhesive, such as glue, or by heat, pressure, ultrasonics, etc. The adhesive can be either water-soluble or water-insoluble. A water-soluble adhesive is preferred for environmental reasons in that the wall 24 will quickly break apart when it is immersed in water. Such immersion will occur should the first member 14 be disposed of by flushing it down a toilet. Exposure of the first member 14 to a municipal's waste treatment plant wherein soaking in water, interaction with chemicals and agitation all occur, will cause the wall 24 to break apart and even dissolve in a relatively short period of time.

The inside diameter of the first member 14 is usually less than about 0.75 inches (about 19 mm) and preferably less than about 0.625 inches (about 16 mm). Although the exterior diameter of tampons do vary, most tampons utilized by women have an external diameter of less than about 0.75 inches (about 19 mm).

The first member 14 is sized and configured to house the absorbent tampon 22. As stated above, the first member 14 should have a substantially smooth exterior surface 26 which will facilitate insertion of the first member 14 into a woman's vagina. When the exterior surface 26 is smooth and/or slippery, the first member 14 will easily slide into a woman's vagina without subjecting the internal tissues of the vagina to abrasion. The first member 14 can be coated to give it a high slip characteristic. Wax, polyethylene, a combination of wax and polyethylene, cellophane and clay are representative coatings that can be applied to the first member 14 to facilitate comfortable insertion.

The first member 14 can be a straight, elongated cylindrical tube formed on a central longitudinal axis X—X (see FIG. 2). It is also possible to form the first member 14 into an arcuate shape. The arcuate or curved shape can assist in providing comfort when inserting the first member 14 into a woman's vagina. With a curved tampon applicator, it is possible to employ a curved tampon which again may be more comfortable for some women to use since the shape of the tampon may better fit the curvature of a woman's vagina.

Referring to FIG. 1, an insertion tip 32 is shown having a plurality of pleats or petals 36 that can radially open such that the insertion tip 32 has a diameter approximately equal to or greater than the diameter of the first member 14. The pleats 36 can be either even or odd in number and can be equally spaced apart or non-uniformly arranged.

Referring again to FIGS. 1 and 2, the first member 14 can have a fingergrip ring 40 located approximate the second end 30. The fingergrip ring 40 can be integrally formed from the material from which the first member 14 is constructed or it can be a separate member that is secured in place by an adhesive or some other type of attachment mechanism. The fingergrip ring 40 functions to provide a means for the user to grip the first member 14 and hold it between her thumb and middle finger. The user can then position her forefinger on the free end of the second member 18 and orient the first member 14 relative to her vagina while she pushes the second member 18 into the first member 14.

As stated above, the tampon applicator 10 includes a second member 18, also commonly referred to as an inner tube. The second member 18, like the first member 14, can be a spirally wound, a convolutely wound or a longitudinally seamed hollow tube constructed from paper, paperboard, cardboard, other suitable material, or a combination thereof. The second member 18 can also be seamlessly formed of plastic. Any plastic in the second member 18 is preferably polyethylene, but may be polypropylene or other suitable plastic. The second member 18 can be constructed of the same material as the first member 14 or it can be made out of a different material. The second member 18 may also be a solid stick or use some other unique shape. It is also possible to form a fingergrip ring or flange 44 on the outer end of the second member 18 to provide an enlarged surface onto which the user's forefinger can rest. The fingergrip ring 44 thereby functions as a seat for the forefinger and facilitates movement of the second member 18 into the first member 14.

In an alternate embodiment (not shown), the first member 14 and second member 18 of the tampon applicator 10 may be replaced by a stick applicator. The stick applicator is used to insert the tampon 22, after which the stick applicator is withdrawn.

A tampon 22 is an absorbent member primarily designed to be worn by a woman during her menstrual period to absorb menses, blood, and other body fluids. A tampon may be also worn by a woman during other phases of the menstrual cycle, as would be the case in the invention described herein if the symptoms or conditions to be treated manifest themselves at a time other than during her menstrual period.

The tampon 22 includes a tampon body 50 and a withdrawal string 54. The tampon body 50 is normally compressed into the form of a cylinder and can have a blunt, rounded or shaped forward or distal end. The tampon body 50 has a forward or distal end 58 that is closer to the cervix when the tampon 22 is in use. The tampon body 50 also has a proximal end 62 that is closer to the vaginal opening when the tampon 22 is in use. The tampon body 50 includes an application zone 66 and an absorbency zone 70, where the application zone 66 is generally located adjacent the proximal end 62 of the tampon body 50, and the absorbency zone 70 is generally located adjacent the distal end 58 of the tampon body 50. The application zone 66 preferably includes absorbent material, but the application zone 66 may also be partially or substantially composed of non-absorbent material.

In alternate embodiments (not shown), the application zone 66 and the absorbency zone 70 are not necessarily adjacent to each other; a neutral zone may be positioned between the absorbency zone 70 and the application zone 66. Also, more than one application zone 66 may be alternated, either axially or radially, with more then one neutral zone.

The tampon 22 commonly has a withdrawal string 54 fastened to the proximal end 62 that serves as a means for withdrawing the tampon from the woman's vagina. The withdrawal string 54 can be looped through an aperture 74 formed transversely through the tampon body 50. In addition, the withdrawal string 54 can have a knot 78 formed at the free end of the string to assure that the string 54 will not separate from the tampon body 50.

Catamenial tampons suitable for use in the present invention include an absorbent. The absorbent can be formed from fibers that are assembled into an absorbent sheet or ribbon. Alternatively, the absorbent can be formed from absorbent fibers that are assembled and compressed into a generally elongated and/or cylindrical configuration. The absorbent is desirably formed from cellulosic fibers, such as cotton and rayon. For example, the absorbent can be 100% cotton, 100% rayon, a blend of cotton and rayon fibers, or other materials known to be suitable for tampons, including artificial fibers such as polyester, polypropylene, nylon or blends thereof. The absorbent may also include degradable fibers. Other types of materials or structures may also be used, such as cellulose sponge or a sponge formed from elastomeric materials. When formed, the absorbent typically includes interstitial space or voids between the fibers or other materials.

Tampons suitable for use in this invention are usually made of absorbent fibers, including one or both of natural and synthetic fibers, compressed into a unitary body of a size that may easily be inserted into the vaginal cavity. Fiber orientation is typically in a linearly- or radially-wound structure. Tampons are normally made in an elongated cylindrical form in order that they may have a sufficiently large body of material to provide the required absorbing capacity, but may be made in a variety of shapes. The tampon 22 is typically compressed. Compression may be achieved by predominantly axially- or radially-applied pressure. The tampon 22 may be made of various fiber blends including both absorbent and nonabsorbent fibers, which may or may not have a suitable cover or wrapper. The cover or wrapper for absorbent products, such as tampons and sanitary napkins, is often made from a sheet of spunbonded fibers, e.g., a spunbond polypropylene sheet. The tampon may also include one or more of various treatments to improve the performance of the tampon, including reduced friction and increased absorption, delivery of the therapeutic agent, or both.

The fibers from which the present absorbent products are made may be produced, for example, by the meltblowing or spunbonding processes, including those producing bicomponent, biconstituent, or polymer blend fibers that are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above. The manufacture of spunbond and meltblown webs is discussed generally above.

As mentioned, the nonwoven also may be a bonded carded web. Bonded carded webs are made from staple fibers, which are usually purchased in bales. The bales are placed in a picker, which separates the fibers. The fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

An exemplary absorbent material is a nonwoven web composed of 3.0 denier polyethylene sheath/polypropylene core bicomponent staple fibers having a length of 38 millimeters. Such bicomponent fibers can be obtained from Chisso Corporation and are typically supplied with a vendor fiber finish or other treatments. The staple fibers can be sent through an opener and uniformly mixed together before being carded into a web at a line speed of 15.24 meters per minute (50 feet per minute). Once the web is formed, it can be sent through a through-air bonder (drum type) with an air temperature of 131° C. Typical dwell times within the bonder are between 3 and 4.5 seconds. The resultant web, which has a basis weight of 100 gsm and a density of 0.06 gm/cm$^3$, can then be wound up on a roll.

A therapeutic agent delivery system including a therapeutic agent can be produced integrally with the tampon 22. For the purposes of this invention, any therapeutic agent that will be absorbed into a user's body through the vaginal epithelium for the purposes of treating diseases or conditions such as, for example, dysmenorrhea, can be used. Alternatively, or in addition, therapeutic and other beneficial agents such as vitamins, hormones, moisturizers, antifungal agents, antibacterial agents, pro-biotic agents that promote the growth of normal vaginal bacterial flora, and the like may be similarly delivered.

Therapeutic agents for use in the invention are absorbable through the vaginal epithelium and travel to the uterus by a unique portal of veins and arteries which are known to exist between the vagina, the cervix and the uterus. This anastomosis eliminates so called first pass metabolism by the liver, effectively delivering higher concentrations of therapeutic agent to the uterus than would otherwise be available via oral dosing. One skilled in the art knows the efficacy of therapeutic agents in such an application when introduced at a particular anatomical location. For example, when the therapeutic agent is selected to treat dysmenorrhea, it preferably is selected from the group consisting of nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

COX-2 inhibitors, such as Celecoxib, Meloxicam, Rofecoxib, and Flosulide are novel anti-inflammatory and analgesic compounds. These compounds effectively inhibit production of COX-2 enzyme that is induced by pro-inflammatory stimuli in migratory cells and inflamed tissue. Because COX-2 is also involved in reproductive processes, selective COX-2 inhibitors will reduce uterine contractions in pre-term labor and relieve painful uterine contractions associated with dysmenorrhea by blocking prostaglandin receptors in the uterus. Additionally, they may reduce endometrial bleeding.

Preferred NSAIDs include Aspirin, Ibuprofen, Indomethacin, Phenylbutazone, Bromfenac, Sulindac, Nabumetone, Ketorolac, Mefenamic Acid, and Naproxen. Preferred local anesthetics include Lidocaine, Mepivacaine, Etidocaine, Bupivacaine, 2-Chloroprocaine hydrochloride, Procaine, and Tetracaine hydrochloride. Preferred calcium channel antagonists include Diltaizem, Israpidine, Nimodipine, Felodipine, Verapamil, Nifedipine, Nicardipine, and Bepridil. Preferred potassium channel blockers include Dofetilide, E-4031, Imokalant, Sematilide, Ambasilide, Azimilide, Ted isamil, RP58866, Sotalol, Piroxicam, and Ibutilide. Preferred β-adrenergic agonists include Terbutaline, Salbutamol, Metaproterenol, and Ritodrine. Vasodilators, which are believed to relieve muscle spasm in the uterine muscle, include nitroglycerin, isosorbide dinitrate, and isosorbide mononitrate. COX-2 inhibitors include Celecoxib, Meloxicam, Rofecoxib, and Flosulide.

Examples of beneficial botanicals may include, but are not limited to, *Agnus castus*, aloe vera, comfrey, calendula, dong quai, black cohosh, chamomile, evening primrose, *Hypericum perforatum*, licorice root, black currant seed oil, St. John's wort, tea extracts, lemon balm, capsicum, rosemary, *Areca catechu*, mung bean, borage seed oil, witch hazel, fenugreek, lavender, and soy. *Vaccinium* extracts commonly derived from many members of the heath family, cranberries such as blueberries, and azaleas (*Rhododendron* spp.) as well as from red onion skin and short and long red bell peppers, *Beta vulgaris* (beet) root extract, and capsanthin may also be used. Other berries that have applicability are whortleberry, lingenberry, chokeberry, sweet rowan, rowanberry, seabuckhrouberry, crowberry, strawberries, and gooseberries.

These botanicals can be combined with other beneficial agents including, but are not limited to, vitamins, calcium, magnesium, hormones, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

These beneficial therapeutic agents promote epithelial health in the vaginal region by delivering botanical ingredients with a feminine care device. The idea is to modulate the vaginal environment to enhance the wellness of this anatomical region. These benefits can be rather simple, for example increasing comfort by providing moisturization and/or lubricity. These benefits can also be more complex, for example modulating epithelial cell function to address vaginal atrophy. The beneficial therapeutic agents may reduce negative sensations such as stinging, burning, itching, etc, or introduce positive sensations to improve comfort.

For example, many therapeutic benefits have been ascribed to a large number of different botanical preparations. Preparations may include water-in-oil emulsions, oil-in-water emulsions, gel, liquid, dispersion, powder, and anhydrous systems, ointment, or salve, such as a botanical oil in an anhydrous base (e.g., petrolatum), or polyethylene glycol based systems. Also, botanicals are often prepared or extracted under conditions to generate water-soluble or oil-soluble extracts. These extracts are usually compositionally different and may have different skin and vaginal health benefits. Processing conditions will have an effect on the type of formulation that can be used and this will restrict the type of botanical (water or oil type) selected. Therefore, wide ranges of botanicals have utility in this invention. Botanicals can possess a variety of actives and activities that can include, but are not necessarily limited to, analgesics, antimicrobials, pro-biotic agents, anti-inflammatory compounds, anti-virals, enzymes, enzyme inhibitors, enzyme substrates, enzyme cofactors, ions, ion chelators, lipids, lipid analogs, lipid precursors, hormones, inflammatory mediators, inflammatory agonists, oxidants, antioxidants, humectants, growth factors, sugars, oligosaccarides, polysaccarides, vasodilators, and potential combinations thereof. It is understood that, for the purposes of this invention, the botanicals can be combined with any number of non-botanical active ingredients as well.

The therapeutic agent delivery system may also include carrier components to promote the functionality of the therapeutic agent. For example, the carrier components may assist the therapeutic agent in absorbing into, or adhering onto, the tampon body 50. The carrier components may assist the release of the therapeutic agent from the tampon body 50, or assist in the absorbency of the therapeutic agent into the vaginal epithelium. The use of excipients to facilitate the formulation, delivery, stability, and aesthetic properties of a drug delivery system is well known to those familiar with the art.

In one embodiment, the therapeutic agent and the therapeutic agent delivery system are applied to the outer surface 82 of the tampon body 50, substantially within the application zone 66 and predominantly to the surfaces that will be in contact with the vaginal epithelium. In an alternate embodiment, the formulation including a therapeutic agent may be applied to a pledget, a portion of a pledget, or to a combination of outer surface and pledget. In another alternate embodiment, the formulation including a therapeutic agent may be applied to degradable fibers in or on the tampon body 50. In still another embodiment, the formulation including a therapeutic agent may be interspersed through the interstitial space in the absorbent.

As an example, the catamenial tampon 22 includes a permeable cover sheet that contains a therapeutic agent. In this example, such a tampon 22 would have a cover sheet formed from spunbond fibers of a hydrophobic polymeric material, e.g., a spunbond polypropylene cover layer, with a therapeutic agent coated on the outside of the fibers.

It may not be necessary to impregnate the entire absorbent body of an absorbent product, such as a tampon 22, with the therapeutic agent. Optimum results both economically and functionally, can often be obtained by concentrating the material on or near an outer surface where it will be most effective during use.

The formulation including a therapeutic agent may be applied to the absorbent article using conventional methods for applying a therapeutic agent to the desired absorbent article. For example, unitary tampons may be dipped directly into a bath having the agent and then can be dried. A formulation including a therapeutic agent may be applied after the tampon is compressed. The formulation including a therapeutic agent, when incorporated on and/or into the tampon materials, may be fugitive, loosely adhered, bound, or any combination thereof. As used herein the term "fugitive" means that the formulation including a therapeutic agent is capable of migrating through the tampon materials. For example, a therapeutic agent may be blended together with a polymeric material that is to be processed into a component of an absorbent or non-absorbent product.

Alternatively, a formulation including a therapeutic agent may be applied directly onto an individual layer of material before it is incorporated into an article to be manufactured, such as an absorbent product. For example, an aqueous solution containing a therapeutic agent can be applied by any method known in the art onto the surface of a porous cover sheet or absorbent layer designed to be incorporated into an absorbent product. This can be done either during the production of the individual layer or during a fabrication process that incorporates the layer into the article being manufactured.

Nonwoven webs coated with a formulation including a therapeutic agent can be prepared by conventional processes. For example, a formulation including a therapeutic agent can be applied to one or both sides of a traveling web. Those skilled in the art will appreciate that the application can be carried out as an inline treatment or as a separate, offline treatment step. A web, such as a spunbond or meltblown nonwoven, can be directed over support rolls to a treating station including rotary spray heads for application to one side of web. An optional treating station may include rotary spray heads to apply a formulation including a therapeutic agent to the opposite side of the web. Each treatment station generally receives a supply of treating liquid from a reservoir. The treated web may then be dried if needed by passing over dryer cans or other drying means and then wound as a roll or converted to the use for which it is intended. Alternative drying apparatus such as ovens, through air dryers, infra red dryers, air blowers, and the like may also be utilized.

Active ingredients, such as pharmaceutical compounds (e.g., histidines, anti-inflammatory drugs, calcium or potassium channel blockers), antimicrobials, anesthetics, hormones or hormone inhibitors, pH control agents, and the like, can be provided in any known drug delivery medium that is placed within the tampon. An example is microencapsulation of the active ingredient in starch, dextran, or other degradable or soluble materials, such that microcapsules placed in the absorbent material of the tampon can permit gradual release of the active ingredient upon wetting, an increase in temperature, or physical contact. Another type of delivery system is the use of polymeric transport systems, which are materials that absorb materials and will release these materials when applied to a substrate.

Combining the active ingredient with a hydrophobic material such as a solidifying agent; wax, solid ester, solid fatty alcohol or acid, hydrogenated vegetable oil, solid triglycerides, natural soft solid materials (i.e., cocoa butter), solid alkyl silicones, and the like, allows gradual diffusion of the active ingredient from the hydrophobic material to the body of the wearer, while preventing loss of the active ingredient during gushing of body fluids. In one embodiment, the solidifying agent can be solid at room temperature but can soften at body temperature to increase the release rate of the active ingredient once the product has been in contact with the body for a period of time.

The active ingredient may be combined with a hydrogel material. Upon wetting, the hydrogel material swells, resulting in increased delivery of the active ingredient from the swollen material.

The active ingredient may also be combined with a substantially hydrophobic emollient or lotion that can resist being washed away by aqueous body fluids but which can nevertheless transfer to body surfaces during use to enhance drug delivery.

Another example is the use of polyethylene glycols with molecular weights greater than 720 as solidifying agents. The active ingredient can be solubilized or dispersed in polyethylene glycols, which are water dispersible materials. Contact with water containing body fluids will slowly dissolve the polyethylene glycol and release the active ingredient to the body surface.

Finally, the active ingredient may be placed within a pouch in the tampon, which can release active ingredients by diffusion through a permeable membrane, rupture or degradation of a portion of the wall of the pouch, or active deployment wherein, for example, a material in the pouch or reservoir swells upon wetting and forces expulsion of the active ingredient, or a foam is generated to carry the active ingredient out of the pouch.

Nonwoven or film components such as a liquid-pervious cover layer or other component can also be combined with active ingredients in a variety of means. The active ingredient can be attached to the surface of the nonwoven or film, or may be incorporated into the solid matrix. For example, an active ingredient can be blended in one or more polymer phases prior to manufacture of the nonwoven or film, or can be added into the solid phase as a post treatment by a variety of means, including delivery in a supercritical fluid carrier. With polyolefin polymers and other compounds, the presence of supercritical carbon dioxide, for example, causes substantial swelling of the polymer, creating large pore spaces in the swollen state into which an active ingredient can diffuse. Removal of the supercritical carbon dioxide then causes reversal of the swelling, resulting in trapping of the active ingredient within the solid matrix of the nonwoven or film, with the possibility for gradual release of the active ingredient from the matrix when in contact with biological membranes or fluids, especially upon wetting.

Alternately, vehicles with various degrees of complexity can be used ranging from simple vehicles made of a singular substance to gels, liquids, emulsions, solids, powders or to even more complex vehicles such as those containing liposomes or particulate materials bearing specific ligands with which to target the agent to particular locations within the vaginal environment. In other embodiments, the device could include degradable hollow fibers or other structures wherein the cavity is filled with the agent. In this way the material would be released only in response to specific events. In still other embodiments, the absorption of the therapeutic agent can be augmented with penetration enhancers.

Apertured webs can also be used to contain an active ingredient, either as a substrate or component in a laminated structure. The webs that can be used include those of Tredegar Corp. and AET Specialty Nets & Nonwovens, including the latter's includes DELNET-brand geometric apertured fabrics, DELNET-EP-brand coextruded adhesive fabrics, PLASTINET-brand biplanar netting and sleeving, STRATEX-brand engineered laminated structures, and DELPORE-brand, DELGUARD-brand and DELSORB-brand meltblown nonwoven fabrics, any of which can be treated with or combined with active ingredients. Active ingredients can also be provided as an internal component of a laminated structure, such as a central layer in a laminate between two film layers.

Foam components can also be combined with active ingredients. Active ingredients can be directly mixed with the solid matter forming the matrix of the foam, or can be contained as a solid phase such as particulates or as a viscous phase within the open or enclosed cells of the foam. Release of the active ingredient can occur upon wetting, wither by solvating the active ingredient from the solid matrix, dissolving the walls of an encapsulating medium, or permitting a diffusion pathway back to mucosal membranes. Foam matrices can include regenerated cellulose; synthetic polymers such as polyurethane; gelatin or other protein-based compositions such as those derived from albumin; High-Internal-Phase-Ratio Emulsions (HIPE) technology such as that disclosed in U.S. Pat. No. 5,652,194, "Process for Making Thin-Wet Absorbent Foam Materials for Aqueous Body Fluids," issued Jul. 29, 1997 to Dyer et al.; and fiber-based foam compositions such as those disclosed in U.S. Pat. No. 6,261,679, "Fibrous Absorbent Material and Methods of Making the Same," issued Jul. 17, 2001 to F-J. Chen et al.

Cellulose fibers can be combined with active ingredients in a variety of ways, including attachment by chemical or physiochemical means such as van der Waals forces, covalent bonds or ionic bonds; physical entanglement (being mechanically trapped by the porous structure); or lumen loading, wherein the active ingredient is chemically or mechanically deposited into the hollow lumen or core of a natural cellulose fiber or a synthetic fiber, as disclosed in U.S. Pat. No. 4,510,020, issued to H. V. Green et al., Apr. 9, 1985; or U.S. Pat. No. 5,096,539, issued to G. G. Allan, Mar. 17, 1992. The same can be done for hollow non-cellulose fibers. Cellulose webs can also be impregnated or coated with active ingredients, either alone or in combination with hydrophobic matter, hydrogels, or other carriers, as disclosed, for example, in U.S. Pat. No. 5,990,377, "Dual-zoned Absorbent Webs," issued Nov. 23, 1999 to F-J. Chen et al.

Active ingredients can also be combined with an active deployment means that physically moves the active ingredient after being triggered by wetting or an increase in temperature. For example, the active deployment means can comprise generation of foam or bubbles in an effervescent effect that can move the active ingredient from within the absorbent article toward the body of the user, triggered by contact with an aqueous fluid, for example. A swellable material placed with the active ingredient in a pouch with a liquid-pervious inelastic wall can swell upon wetting and force expulsion of the active ingredient from the pouch.

In an alternate embodiment, a reservoir 86 within the application zone 66 is provided in which to locate the therapeutic agent. The agent may be stored within the reservoir in various forms and in varying dosages. For example, the agent may be placed in the reservoir 86 in liquid form, in solid form, or in an encapsulated form. The agent may be formulated to act immediately upon insertion of the tampon 22, or in a time-release manner. The agent may be activated by pressure from the insertion, or from pressure, heat, or humidity in the vaginal environment. The agent may be placed by the manufacturer of the tampon or the tampon user as needed.

For example, and in reference to FIG. 2, the agent may be encapsulated 90 and located within the application zone 66. Insertion pressure on the tampon body 50 from the second member 18 ruptures the capsule 90, releasing the agent into the surrounding tampon material and thus to the vaginal epithelium.

In another alternate embodiment, the agent may be formed into a generally toroidal, disc, or other suitable shape and positioned at the proximal end 62 of the tampon body 50. The agent may be positioned by the manufacturer or by a tampon user when needed.

The therapeutic agent may be combined into a formulation that may contain other additives or carrier components as appropriate for the desired result so long as the additives or carrier components do not have a major detrimental effect on the activity of the therapeutic agent. Examples of such additives include additional conventional surfactants, such as esters like myreth-3-myristate, ethoxylated hydrocarbons, or ionic surfactants, or co-wetting aids such as low molecular weight alcohols. The formulation is desirably applied from high solids, advantageously 80% or less solvent or water, so as to minimize drying and its attendant costs and deleterious effects. The treating formulation including a therapeutic agent may be applied in varying amounts depending on the desired results and application. Those skilled in the art can readily select the actual amount based on the teaching of this application. For example, a catamenial tampon 22 designed to be inserted into a body cavity and subsequently in intimate contact with the vaginal epithelium may require substantially less therapeutic agent than an absorbent article worn exterior to the body due to the absence of first pass liver metabolism as previously discussed.

It will be recognized by those skilled in this art that a therapeutic agent may be used as an internal additive, that is, added to the polymer melt directly or in a concentrate form. After fiber formation, such additives can migrate to the fiber surface and impart the desired effect. For further discussion of internal addition of additives, see for example, U.S. Pat. No. 5,540,979, the contents of which are incorporated herein by reference. The substrate basis weight is not critical and may vary widely depending on the application. The thermal and oxidation stability of the therapeutic agent must be compatible with the temperature and rheology required for melt processing.

The formulation including a therapeutic agent of the present invention can be prepared and applied in other suitable forms, including without limitation, aqueous solutions, emulsions, lotions, balms, gels, salves, powders, ointments, muco-adhesives, boluses, suppositories, and the like. The formulations of this invention may also contain preservatives. Compounds that can impart greater viscosity, such as polyethylene glycol and the like, may also be added to the formulations of this invention. Generally, higher viscosity formulations are preferred to create formulations that will tend to remain in the vagina for a relatively long time period after administration.

A formulation including a therapeutic agent may additionally employ one or more conventional pharmaceutically-acceptable and compatible carrier materials useful for the desired application. The carrier can be capable of co-dissolving or suspending the materials used in the formulation including a therapeutic agent. Carrier materials suitable for use in the instant formulation including a therapeutic agent, therefore, include those well-known for use in the pharmaceutical, cosmetic, and medical arts as a basis for ointments, lotions, creams, salves, aerosols, suppositories, gels and the like.

In use, and referring to FIG. 2, the applicator 10 functions because the second member 18 is telescopically movable relative to the first member 14. As the second member 18 is pushed into the first member 14, the tampon 22 is forced forward against the pleats or petals 36. The contact by the tampon 22 causes the pleats 36 to radially open to a diameter that is sufficient to allow the tampon 22 to be expelled from the first member 14. With the tampon 22 properly positioned in the woman's vaginal cavity, the tampon applicator 10 is withdrawn and properly discarded.

Once the tampon 22 is properly positioned in the woman's vaginal cavity, The absorbency zone 70 of the tampon body 50 may absorb menses and other bodily fluids, and the application zone 66 of the tampon body 50 may deliver the therapeutic agent to the vaginal epithelium. From there, the therapeutic agent is transferred to the uterus by normal bodily functions to relieve the condition such as dysmenorrhea.

The invention has been described with reference to various specific and illustrative embodiments and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. An absorbent device adapted to deliver a therapeutic agent to a user having a vaginal epithelium, the device comprising:
    a generally cylindrical body having a proximal end and a distal end and adapted to be positioned entirely within the user, the body including
        an absorbency zone adjacent the distal end, wherein the absorbency zone includes absorbent material;
        an application zone adjacent the proximal end and spaced apart from the distal end, wherein the application zone has a surface adapted to contact the vaginal epithelium; and
        a formulation including a therapeutic agent positioned substantially adjacent the surface and substantially within the application zone, wherein the formulation including a therapeutic agent includes a hydrogel material or a foam component.

2. The device of claim 1, wherein the device is a catamenial device.

3. The device of claim 1, wherein the device is an incontinence device.

4. The device of claim 1, wherein the device is a tampon.

5. The device of claim 1, wherein the application zone includes absorbent material.

6. The device of claim 1, wherein the application zone includes non-absorbent material.

7. The device of claim 1, further comprising a reservoir within the application zone, wherein the formulation including the therapeutic agent is located substantially within the reservoir.

8. The device of claim 7, wherein the reservoir is in communication with the application zone surface.

9. The device of claim 7, wherein the reservoir is located under the application zone surface.

10. The device of claim 1, wherein the formulation including a therapeutic agent is encapsulated.

11. The device of claim 1, wherein the body is compressed, and wherein the formulation including a therapeutic agent is applied to the body after the body is compressed.

12. The device of claim 1, wherein the body is constructed from a material; and wherein the formulation including a therapeutic agent is applied to the material before the body is constructed.

13. A method for producing a device for delivering a therapeutic agent to a user having a vaginal epithelium, the method comprising:
    manufacturing a tampon having a generally cylindrical body with a distal end, a proximal end, a longitudinal axis, an absorbency zone adjacent the distal end, and an application zone adjacent the proximal end, wherein the body is adapted to be positioned entirely within the user, wherein the absorbency zone has an absorbency zone surface adapted to contact the vaginal epithelium and absorbent material extending from the longitudinal axis to the absorbency zone surface, wherein the application zone has an application zone surface, and wherein the manufacturing act includes manufacturing the body from a material; and
    locating a formulation including a therapeutic agent substantially adjacent the application zone surface and substantially within the application zone, including applying the formulation including a therapeutic agent to the material before the body is manufactured.

14. The method of claim 13, further comprising providing a tampon applicator such that pressure from the tampon applicator on the body releases the therapeutic agent from the application zone.

* * * * *